(12) United States Patent
Kapurniotu et al.

(10) Patent No.: US 6,359,112 B2
(45) Date of Patent: *Mar. 19, 2002

(54) PEPTIDES USED AS AGONISTS AND/OR INHIBITORS OF AMYLOID FORMATION AND CYTOTOXICITY AND ALSO FOR USE IN ALZHEIMER'S DISEASE, IN TYPE II DIABETES MELLITUS AND IN SPONGIFORM ENCEPHALOPHATHIES

(75) Inventors: Afroditi Kapurniotu; Jürgen Bernhagen, both of Tubingen; Herwig Brunner, Stuttgart, all of (DE)

(73) Assignee: Fraunhofer-Gesellschaft zur Forferung der angewandten Forschung e.V., Munich (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/097,194

(22) Filed: Jun. 12, 1998

(30) Foreign Application Priority Data

Jun. 17, 1997 (DE) .......................................... 197 25 619

(51) Int. Cl.⁷ ............................. C07K 4/12; C07K 5/02; C07K 7/00
(52) U.S. Cl. ...................... 530/326; 530/327; 530/328; 530/329; 530/330; 530/331
(58) Field of Search ............................. 530/324–331; 514/12–19

(56) References Cited

U.S. PATENT DOCUMENTS 5,773,572 A * 6/1998 Fishleigh et al.
5,854,204 A * 12/1998 Findeis et al.

FOREIGN PATENT DOCUMENTS

| EP | 0 289 287 A2 | 4/1988 |
| EP | 0 309 100 A2 | 8/1988 |
| WO | WO 96/07425 | 3/1996 |
| WO | WO 96/39834 | 12/1996 |

* cited by examiner

*Primary Examiner*—Marianne P. Allen
(74) *Attorney, Agent, or Firm*—Millen, White, Zelano & Branigan, P.C.

(57) ABSTRACT

Certain peptide molecules can be used as the basic structures (template molecules) for inhibiting and analysing amyloid formation and cytotoxicity in amyloid illnesses. These peptides have an effect on the molecules which are responsible for the amyloid illnesses (for their part amyloid-forming peptides and proteins). The peptides are thus either inhibitors themselves or agonists of amyloid formation and cytotoxicity or can serve as a template for identifying and producing further inhibitors and agonists and can be used as molecular tools during analysis. The peptide molecules have generally 3–15 amino acids, and preferably a maximum of 10 amino acids, and at least an active peptide sequence GA, preferably GAI, and even more preferably one selected from the group consisting of GAIL, SEQ ID NO: 1; FGAIL, SEQ ID NO: 2; NFGAIL, SEQ ID NO: 3; NNFGAIL, SEQ ID NO: 4; SNNFGAIL, SEQ ID NO: 5; NFGAILSS, SEQ ID NO: 6; SNNFGAILSS, SEQ NO: 7; or the group consisting of GAII, SEQ ID NO: 8; KGAII, SEQ ID NO: 9; NKGAII, SEQ ID NO: 10; SNKGAII, SEQ ID NO: 11; GSNKGAII, SEQ ID NO: 12; NKGAIIGL, SEQ ID NO: 13; GSNKGAIIGL, SEQ ID NO: 14; or the group consisting of GAVV, SEQ ID NO: 15; AGAVV, SEQ ID NO: 16; VAAGAVV, SEQ ID NO: 17; HVAAGAVV, SEQ ID NO: 18; AAGAVVGG, SEQ ID NO: 19; HVAAGAVVGG, SEQ ID NO: 20; AAGAVV, SEQ ID NO: 21. The peptide sequence generally has at least one hydrogen molecule, and preferably every second hydrogen molecule, of an amide bond replaced by a methyl group.

10 Claims, 4 Drawing Sheets

FIG. 1

Arrangement of homologous sequences of IAPP, β-AP and the prion protein (PrP). Homologous residues are <u>underlined</u>: conservative substitutions are in bold.

Sequence (20-29) of hIAPP:    S N <u>N</u> F <u>G</u> <u>A</u> I L S S

Sequence (25-34) of β-IAPP:    G S <u>N</u> K <u>G</u> <u>A</u> I I <u>G</u> L Sequence (110-119) of PrP:    H V A A <u>G</u> <u>A</u> V V <u>G</u> G

SEQUENCE LISTING

<160> NUMBER OF SEQ ID NOS: 21

<210> SEQ ID NO 1
<211> LENGTH: 4
<212> TYPE: PRT
<213> ORGANISM: Homo sapiens

<400> SEQUENCE: 1

Gly Ala Ile Leu
1

<210> SEQ ID NO 2
<211> LENGTH: 5
<212> TYPE: PRT
<213> ORGANISM: Homo sapiens

<400> SEQUENCE: 2

Phe Gly Ala Ile Leu
1               5

<210> SEQ ID NO 3
<211> LENGTH: 6
<212> TYPE: PRT
<213> ORGANISM: Homo sapiens

<400> SEQUENCE: 3

Asn Phe Gly Ala Ile Leu
1               5

<210> SEQ ID NO 4
<211> LENGTH: 7
<212> TYPE: PRT
<213> ORGANISM: Homo sapiens

<400> SEQUENCE: 4

Asn Asn Phe Gly Ala Ile Leu
1               5

-continued

```
<210> SEQ ID NO 5
<211> LENGTH: 8
<212> TYPE: PRT
<213> ORGANISM: Homo sapiens

<400> SEQUENCE: 5

Ser Asn Asn Phe Gly Ala Ile Leu
  1               5

<210> SEQ ID NO 6
<211> LENGTH: 8
<212> TYPE: PRT
<213> ORGANISM: Homo sapiens

<400> SEQUENCE: 6

Asn Phe Gly Ala Ile Leu Ser Ser
  1               5

<210> SEQ ID NO 7
<211> LENGTH: 10
<212> TYPE: PRT
<213> ORGANISM: Homo sapiens

<400> SEQUENCE: 7

Ser Asn Asn Phe Gly Ala Ile Leu Ser Ser
  1               5                  10

<210> SEQ ID NO 8
<211> LENGTH: 4
<212> TYPE: PRT
<213> ORGANISM: Homo sapiens

<400> SEQUENCE: 8

Gly Ala Ile Ile
  1

<210> SEQ ID NO 9
<211> LENGTH: 5
<212> TYPE: PRT
<213> ORGANISM: Homo sapiens

<400> SEQUENCE: 9

Lys Gly Ala Ile Ile
  1               5

<210> SEQ ID NO 10
<211> LENGTH: 6
<212> TYPE: PRT
<213> ORGANISM: Homo sapiens

<400> SEQUENCE: 10

Asn Lys Gly Ala Ile Ile
  1               5

<210> SEQ ID NO 11
<211> LENGTH: 7
<212> TYPE: PRT
<213> ORGANISM: Homo sapiens

<400> SEQUENCE: 11

Ser Asn Lys Gly Ala Ile Ile
  1               5

<210> SEQ ID NO 12
<211> LENGTH: 8
```

```
<212> TYPE: PRT
<213> ORGANISM: Homo sapiens

<400> SEQUENCE: 12

Gly Ser Asn Lys Gly Ala Ile Ile
 1               5

<210> SEQ ID NO 13
<211> LENGTH: 8
<212> TYPE: PRT
<213> ORGANISM: Homo sapiens

<400> SEQUENCE: 13

Asn Lys Gly Ala Ile Ile Gly Leu
 1               5

<210> SEQ ID NO 14
<211> LENGTH: 10
<212> TYPE: PRT
<213> ORGANISM: Homo sapiens

<400> SEQUENCE: 14

Gly Ser Asn Lys Gly Ala Ile Ile Gly Leu
 1               5                  10

<210> SEQ ID NO 15
<211> LENGTH: 4
<212> TYPE: PRT
<213> ORGANISM: Homo sapiens

<400> SEQUENCE: 15

Gly Ala Val Val
 1

<210> SEQ ID NO 16
<211> LENGTH: 5
<212> TYPE: PRT
<213> ORGANISM: Homo sapiens

<400> SEQUENCE: 16

Ala Gly Ala Val Val
 1               5

<210> SEQ ID NO 17
<211> LENGTH: 7
<212> TYPE: PRT
<213> ORGANISM: Homo sapiens

<400> SEQUENCE: 17

Val Ala Ala Gly Ala Val Val
 1               5

<210> SEQ ID NO 18
<211> LENGTH: 8
<212> TYPE: PRT
<213> ORGANISM: Homo sapiens

<400> SEQUENCE: 18

His Val Ala Ala Gly Ala Val Val
 1               5

<210> SEQ ID NO 19
<211> LENGTH: 8
<212> TYPE: PRT
<213> ORGANISM: Homo sapiens
```

```
<400> SEQUENCE: 19

Ala Ala Gly Ala Val Val Gly Gly
  1               5

<210> SEQ ID NO 20
<211> LENGTH: 10
<212> TYPE: PRT
<213> ORGANISM: Homo sapiens

<400> SEQUENCE: 20

His Val Ala Ala Gly Ala Val Val Gly Gly
  1               5                  10

<210> SEQ ID NO 21
<211> LENGTH: 6
<212> TYPE: PRT
<213> ORGANISM: Homo sapiens

<400> SEQUENCE: 21

Ala Ala Gly Ala Val Val
  1               5
```

PEPTIDES USED AS AGONISTS AND/OR INHIBITORS OF AMYLOID FORMATION AND CYTOTOXICITY AND ALSO FOR USE IN ALZHEIMER'S DISEASE, IN TYPE II DIABETES MELLITUS AND IN SPONGIFORM ENCEPHALOPHATHIES

BACKGROUND OF THE INVENTION

The invention relates to peptides with 3–15 amino acids which function as agonists and/or inhibitors in amyloid formation and/or toxicity and which can be therefore used in various related clinical pictures.

New strategies and active agents for the therapy and diagnosis of the above-mentioned amyloid illnesses are being researched world-wide. However, there is still no means of treating these illnesses with medicines/pharmaceuticals. According to predominant expert opinion, certain amyloid proteins, which are specific to each illness, are causally responsible for the occurrence of amyloid illnesses because of their amyloid genesis or aggregation. The mechanism for amyloid genesis and the associated cell death (cytotoxicity) in these illnesses is widely unknown and correspondingly, highly specific inhibitors have hence not been identified. Pharmaceuticals for treating amyloid illnesses on the basis of such inhibitors have therefore also not been developed.

In exactly the same way, the protein-chemical, technical-analytical problems, which are caused by amyloid formation, (formation of insoluble protein aggregates, so-called amyloid structures) have up to now not permitted the analysis of amyloid formation. This has contributed to the fact that the mechanism for amyloid formation is still widely unexplained. For analysing the formation of amyloids, constructive diagnostic methods (fast in vitro tests for evaluating the amount, duration and quality of the amyloid structures) still therefore do not exist either. For example, a diagnosis for Alzheimer's can only be performed symptomatically (increasing forgetfulness or similar) or post mortem. Reliable blood tests, for example, cannot be performed during the lifetime of the patient.

On this basis it is therefore the object of the invention to propose appropriate peptides, which can function as agonists and/or inhibitors of amyloid formation and/or cytotoxicity.

SUMMARY OF THE INVENTION

According to the invention, peptides with 3–15 amino acids are proposed, which contain at least the active sequence GA. It has been shown, that these peptide molecules function as inhibitors and/or agonists of those amyloid peptides/proteins, which cause the amyloid illnesses Alzheimer's disease, Type II diabetes mellitus and spongiform encephalopathies (Creutzfeld Jacob disease, scrapie, BSE). The peptide molecules according to the invention are in a position to inhibit the amyloid genesis or aggregation of the amyloid peptides/proteins of amyloid peptide or β-AP (in Alzheimer's disease), amyline/IAPP (in Type II diabetes mellitus) and prion protein (in spongiform encephalopathies). When inhibition of the amyloid genesis of illness-inducing peptides/proteins is achieved, the cytotoxic effect, which is caused by aggregation of β-AP, amyline/IAPP or prion protein, on tissue cells is inhibited.

The invention offers the following advantages relative to the state of the art:

Simple chemosynthesis to a high degree of purity, and use, according to current methods, of fixed phase peptide synthesis (the peptides described here are shorter, as a rule, than the potential inhibitors described up till now and consist of only one type of chemical component [=amino acids]).

high biological stability, which can be increased even more by the simple chemical inclusion of unnatural amino acids.

broad biological and therefore potentially therapeutic applicability (the high homology level between the corresponding sequences of amyloid-forming peptides/proteins makes possible the overlapping application of inhibitors in all three illnesses).

few side-effects and little antigenicity when used as a therapeutic (the peptides, on the basis of their small size, have a small tendency to induce immune reactions in the patient); other inhibitor candidates which are described in the literature (see above antibodies or higher molecular serum components) are approx. 200–300 times larger than the peptides which are described here.

high biological activity in vitro and thus high predictable biological activity in vivo.

thus high predictability of therapeutic application.

BRIEF DESCRIPTION OF THE DRAWINGS

FIG. 1 is a chart showing the similarity of structure of selected sequences of IAPP, β-AP, and PrP.

DESCRIPTION OF PREFERRED EMBODIMENTS OF INVENTION

Figure 2:
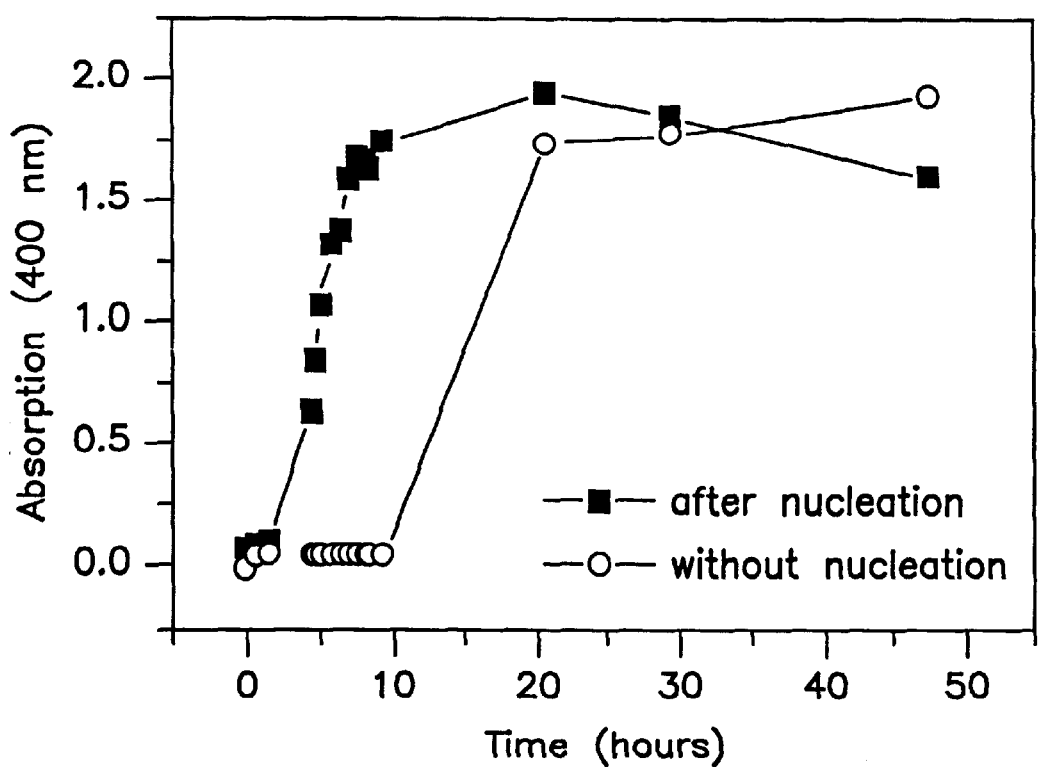
FIG. 2 is a graph of light absorption at 400 nm as a function of time during fibril formation reflecting the aggregation of NFGAIL, SEQ ID NO: 3.

It has been shown that, for the three areas of application described at the beginning, various peptides respectively are particularly appropriate, said peptides all having homology amongst one another (FIG. 1). The individual peptides for the three groups are described subsequently in greater detail.

The appropriate peptide sequence, which is adequate for amyloid formation and cytotoxicity of IAPP, is the sequence FGAIL (one-letter code) SEQ ID NO: 2 which comprises the amino acid residues 23–27 of IAPP. Lengthening this sequence in the direction of the N terminus of IAPP results equally in small (<10 amino acid residues) peptide fragments which can form fibrils (an arranged aggregate structure, which is typical of amyloid illnesses) and has cytotoxicity. For the spontaneous aggregation, i.e. production of an oversaturated peptide solution of these peptides, a concentration is required which is 100–100 times greater compared with IAPP. These sequences were successfully used as small molecular inhibitors of amyloid formation of IAPP, since they contain the shortest peptide sequence and that which is necessary for the aggregation of IAPP. Underlying this effect is the aggregation mechanism of IAPP and, in equal measure, other amyloid forming peptides (such as β-AP and the prion protein). The aggregation and amyloid formation results thus from an intermolecular - folding leaf formation, for which intermolecular (between the molecular chains) hydrogen bonds and hydrophobic reciprocal effects are necessary between the side chains of certain amino acid residues. This -folding leaf structure leads to a non-covalent bond firstly between two and subsequently between several IAPP molecules which consequently form insoluble aggregates/amyloid structures. The effect mechanism (inhibition) of the peptides according to the invention lies in blocking the aggregation-promoting, intermolecular reciprocal effects between two IAPP molecules. By means of this, it has been achieved recently that the peptides themselves are involved in these reciprocal effects with IAPP. Thus competition (agonism) occurs between IAPP and the peptides for the free binding sites of IAPP. Their potential use as illness-diagnostics is also based on the agonistic effect of these peptides. Because of the fact that the soluble form of the peptides or lower concentrations (micromolar) neither aggregate nor have cytotoxicity, their application as inhibitors and Type II diabetes diagnostics is made possible.

The following peptide sequences are synthesised and used as inhibitors of amyloid formation: GAIL, SEQ ID NO: 1; FGAIL, SEQ ID NO: 2; NFGAIL, SEQ ID NO: 3; NNFGAIL, SEQ ID NO: 4; SNNFGAIL, SEQ ID NO: 5; NFGAILSS, SEQ ID NO: 6; SNNFGAILSS, SEQ ID NO: 7; the individual letters for the amino acids exist according to the one letter code. Furthermore, H-molecules of the amide bond of the above peptide sequences are replaced by a methyl group, to block the aggregation of peptides which is induced by—folding leaf formation. The methyl groups were introduced at every second amide bond, however varying the number of methyl groupings. The peptide analogues produced contain a number of N-methyl substituted amide bonds, which extend between one and half of the present amide bonds per molecule. Underlying the design of this class of aggregation inhibitors lies the idea that, by introducing the methyl group at every second amide bond, the dimerisation or the non-covalent bond of the small molecular peptide sequences of IAPP are not impaired; the otherwise consequent non-covalent expansion of the - folding leaf structures, which leads to aggregation, is however comprehensively switched off. In the following, representative examples of this substance class which were used successfully as aggregation inhibitors of IAPP, are named:

(N-Me)-GA-(N-Me) IL, F(N-Me)-GA-(N-Me)IL, NNF (N-Me)-GA-(N-Me)IL, SNNF (N-Me)-GA-(N-Me)IL, NF(N-Me)-GA-(N-Me)ILSS, SNNF (N-Me)-GA-(N-Me)-GA-(N-Me)IL, G(N-Me)-AI(N-Me)-L, FG(N-Me)-AI(N-Me)-L, NNFG (N-Me)-AI(N-Me)-L, SNNFG(N-Me)-AI(N-Me)-L, NFG(N-Me)AI(N-Me)-LSS, SNNFG(N-Me)-AI(N-Me)-LSS, FGA(N-Me)-IL, NFGA(N-Me)-IL, NNFGA(N-Me)-IL, SNNFGA (N-Me)-IL, NFGA(N-Me)-ILSS, SN(N-Me)-NFGAILSS, N-Me)-SN(N-Me)-SN(N-Me)-NFGAILSS, (N-Me)-SN(N-Me)-NF(N-Me)-GAILSS etc.

In the appropriate peptide, which is used for amyloid formation and cytotoxicity of β-AP, sequence regions of β-AP, which are found between the amino acids 25 and 34, are of concern. In analogy to the sequence 23–27 of IAPP, the sequence of 28–32 (KGAII) SEQ ID NO: 9; in β-AP was found to be the appropriate substance for forming amyloids and for neurotoxicity of the entire molecule _-AP. On the basis of the same considerations as in the case of the IAPP amyloid forming inhibitors, the following were synthesised to IAPP homologue β-AP sequences and used as inhibitors of β-AP amyloid formation and β-AP neuro-toxicity: GAII, SEQ ID NO: 8; KGAII, SEQ ID NO: 9; NKGAII, SEQ ID NO: 10; SNKGAII, SEQ ID NO: 11; GSNKGAII, SEQ ID NO: 12; NKGAIIGL, SEQ ID NO: 13; GSNKGAIIGL, SEQ ID NO: 14. Furthermore, as is described above, analogues were also produced with substituted amide bonds. The structures of these analogues were designed according to the same principle as the N-methylated inhibitors of IAPP amyloid formation (see above). Representative examples of this substance class are listed in the following:

(N-Me)GA-(N-Me)II, K(N-Me)-GA-(N-Me)II, NK(N-Me)-GA-(N-Me)II, SNK(N-Me)-GA-(N-Me)II, GSNK (N-Me)-GA-(N-Me)II, NK(N-Me)-GA-(N-Me)IIGL, GSNK(N-Me)-GA-(N-Me)II, G(NMe)AI(N-Me)-I, KG(N-Me)-AI(N-Me)-I, NKG(N-Me)-AI(NMe)-I, SNKG(N-Me)-AI(N-Me)-I, GSNKG(N-Me)-AI(N-Me)-I, NKG(N-Me)-AI(N-Me)-IGL, GSNKG(N-Me)-AI(N-Me)-IGL, KGA(N-Me) -II, NKGA(N-Me)-II, SNKGA(N-Me)-II, GSNKG-A(N-Me)-IIGL, GS(N-Me)-NKGAIIGL, (N-Me)-GS(N-Me) - NKGAIIGL, (N-ME)-GS(N-Me)-GAIIGL etc.

The most suitable sequence, which is adequate for amyloid formation and cytotoxicity of PrP is AGAVV SEQ ID NO: 16. This is to do with a partial sequence from the sequence 110–119 PrP. Further sequences for use as aggregation and toxicity inhibitors of PrP are GAVV, SEQ ID NO: 15; AGAVV, SEQ ID NO: 16; VAAGAVV, SEQ ID NO: 17; HVAAGAVV, SEQ ID NO: 18; AAGAVVGG, SEQ ID NO: 19; HVAAGAVVGG, SEQ ID NO: 20; AAGAVV, SEQ ID NO: 21. The corresponding N-methylated peptide sequences—analagous to the IAPP derivatives (see above)—are also suitable as aggregation and toxicity inhibitors. Some representative examples of N-methylated analogues are presented in the following:

(N-Me)-GA-(N-Me)VV, A(N-Me)-GA-(N-Me)VV, AA(N-Me)-GA-(N-Me)VV, AAGA(N-Me)-VVGG, HV(N-Me)-AAGAVVGG, (N-Me)-HV(N-Me)-AAGAVVGG, (N-Me)HV(N-Me)-AA(N-Me)-GAVVGG etc.

This invention is therefore concerned with peptide molecules which can be used as the basic structures (template molecules) for inhibiting and analysing amyloid formation and cytotoxicity in amyloid illnesses. In this respect, these peptides have an effect on the molecules which are responsible for the amyloid illnesses (for their part amyloid-forming peptides and proteins). The peptides are thus either inhibitors themselves or agonists of amyloid formation and cytotoxicity or can serve as a template for identifying and producing further inhibitors and agonists and can be used as molecular tools during analysis.

These peptides can be used as pharmaceutical inhibitors of amyloid formation and cytotoxicity or as molecular tools for analysing amyloid formation and cytotoxicity in amyloid illnesses. Thus, this is to do with potential pharmaceuticals and analyses for the treatment and diagnosis of the following illnesses which also occur in humans:

Alzheimer's disease
Type II diabetes mellitus
Spongiform encephalopathies
(e.g. Creutzfeld-Jacob disease, scrapie, BSE)
The diagnostic use comprises two aspects:
Use as a molecular tool for further researching the mechanism for amyloid formation in these illnesses (use in research laboratories and R and D laboratories)
Potential use as a reagent for diagnosing amyloid illnesses or the prediction of such illnesses (diagnostic market).

The invention is explained subsequently in greater detail with the aid of an embodiment example.

NFGAIL SEQ ID NO: 3: Production, characterisation, aggregation, testing for fibril formation, testing for cytotoxicity, testing for the inhibitor effect on the aggregation of IAPP.

Production and Characterisation

NFGAIL SEQ ID NO: 3 was produced using current methods of fixed phase peptide synthesis. The Wang anchor was used and the Fmoc/tBu synthesis strategy was adopted. For one 1 mMol application, 4 mMol protected amino acids, 4 mMol of TBTU and 6 mMol of DIEA in DMF were used per coupling step. The splitting of the temporary protected groups (Fmoc) was achieved by means of 25% piperidine in DMF and, in order to split the peptide from the anchor while simultaneously splitting the permanent protected groups of the side chains, 95% TFA was used (reaction time 2 hours). The pipe product was cleaned using preparative RP-HPLC and characterised by FAB-MS and amino acid analysis.

Aggregation and Testing for Fibril Formation

Figure 3:
FIG. 3 is an electron photomicrograph of aggregates of NFGAIL, SEQ ID NO: 3.

The aggregation properties were tested in 10 mM Of phosphate butter pH 7.4. Firstly, a highly concentrated (125–250 mM) parent solution of the peptide in DMSO was produced. The peptide is pipetted from the solution directly into the aggregation solution while being gently stirred. A 5 mM peptide solution aggregated spontaneously and thus did not have an "Aggregation-Lag-Time". On the other hand, aggregate formed only after 9.5 hrs. from a solution of 3.75 mM NFGAIL SEQ ID NO: 3 (Aggregation-Lag-Time: 9.5 hrs) (FIG. 2). Furthermore, aggregation was accomplished immediately, when pre-prepared NFGAIL SEQ ID NO: 3 fibrils (nucleation centres) were added to the 3.75 mM solution (fibril concentration 0.375 mM). It was shown thus, that the aggregation of these peptides operates according to the so-called "nucleation dependent polymerisation mechanism". Recently it has been considered of great importance, since the opinion prevails in the literature, that amyloid formation in vitro should operate using this mechanism. After complete aggregation, the deposit was isolated by centrifuging and examined by electron- and polarisation-microscopy after congo red staining. In this way, the fibrillar and amyloid structure of the aggregate was confirmed (FIG. 3).

Testing for Cytotoxicity

Figure 4:
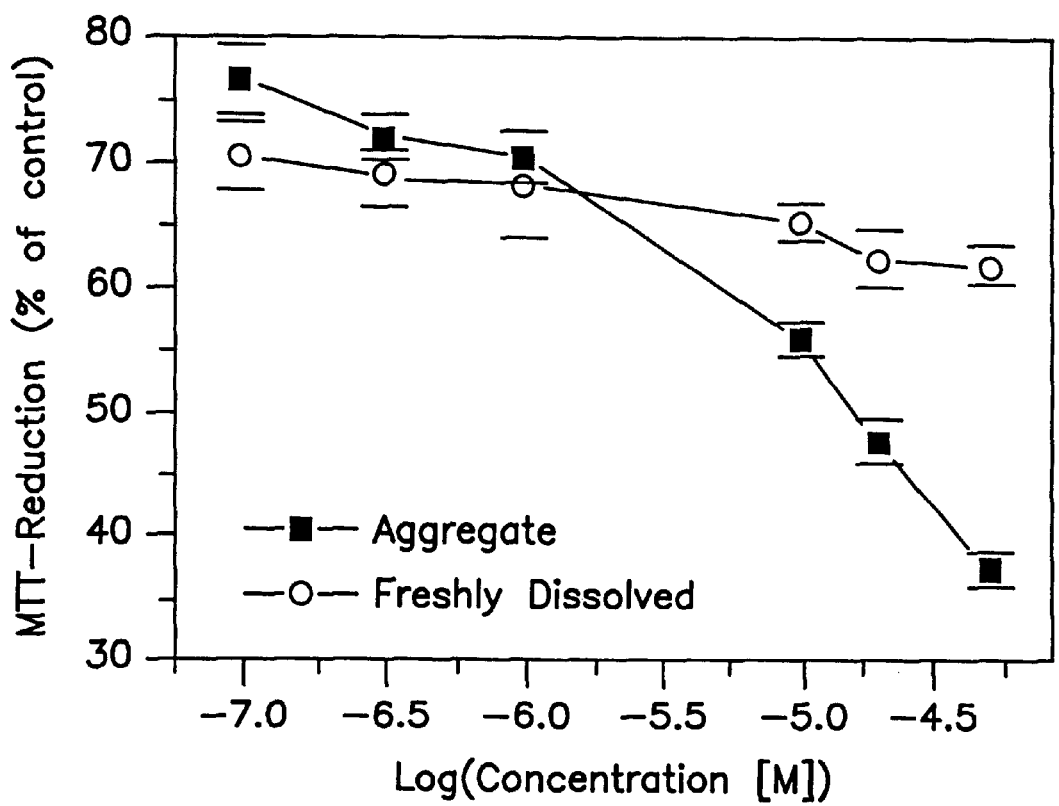
FIG. 4 is a graph of MTT reduction as a function of concentration of NFGAIL, SEQ ID NO: 3.

Suspensions of the peptide aggregate (produced as described as above) were tested by means of a Rat Insulinoma (RIN5 mf) and a human astroglioma-cell series (HTB-14) for toxicity. The newly dissolved peptides were also tested for cytotoxicity. It thus be shown, that the aggregated form of NFGAIL SEQ ID NO: 3 is cyto-toxic, the soluble form of the peptide having no toxicity (FIG. 4).

What is claimed is:

1. A peptide selected from the group consisting of GAIL, SEQ ID NO: 1; FGAIL, SEQ ID NO: 2; NNFGAIL, SEQ ID NO: 4; SNNFGAIL, SEQ ID NO: 5; and NFGAILSS, SEQ ID NO: 6.

2. A peptide selected from the group consisting of GAII, SEQ NO: 8; KGAII, SEQ ID NO: 9; NKGAII, SEQ ID NO: 10; SNKGAII, SEQ ID NO: 11; GSNKGAII, SEQ ID NO: 12; NKGAIIGL, SEQ ID NO: 13; and GSNKGAIIGL, SEQ ID NO: 14.

3. A peptide selected from the group consisting of GAVV, SEQ ID NO: 15; AGAVV, SEQ ID NO: 16; HVAAGAVV, SEQ ID NO: 18; AAGAVVGG, SEQ ID NO: 19; HVAAGAVVGG, SEQ ID NO: 20; and AAGAVV, SEQ ID NO: 21.

4. A peptide comprising 3–15 amino acids and said peptide contains a peptide sequence selected from the group consisting of GAII, SEQ NO: 8; KGAII, SEQ ID NO: 9; NKGAII, SEQ ID NO: 10; SNKGAII, SEQ ID NO: 11; GSNKGAII, SEQ ID NO: 12; NKGAIIGL, SEQ ID NO: 13; and GSNKGAIIGL, SEQ ID NO: 14.

5. A peptide comprising 3–15 amino acids and said peptide contains a peptide sequence selected from the group consisting of HVAAGAVV, SEQ ID NO: 18; and HVAAGAVVGG, SEQ ID NO: 20.

6. A peptide selected from the group consisting of (N-Me)GA(N-Me)IL, F(N-Me)GA(N-Me)IL, NF(N-Me)GA(N-Me)IL, NNF(N-Me)GA(N-Me)IL, SNNF(N-Me)GA(N-Me)IL, NF(N-Me)GA(N-Me)ILSS, SNNF(N-Me)GA(N-Me)GA(N-Me)IL, G(N-Me)AI(N-Me)L, FG(N-Me)AI(N-Me)L, NFG(N-Me)AI(N-Me)L, NNFG(N-Me)AI(N-Me)L, SNNFG(N-Me)AI(N-Me)L, NFG(N-Me)AI(N-Me)LSS, SNNFG(N-Me)AI(N-Me)LSS, FGA(N-Me)IL, NFGA(N-Me)IL, NNFGA(N-Me)IL, SNNFGA(N-Me)IL, NFGA(N-Me)ILSS, SN(N-Me)-NFGAILSS, (N-Me)SN(N-Me)NFGAILSS, and (N-Me)SN(N-Me)NF(N-Me)GAILSS.

7. A peptide selected from the group consisting of (N-Me)GA(N-Me)II, K(N-Me)GA(N-Me)II, NK(N-Me)GA(N-Me)II, SNK(N-Me)GA(N-Me)II, GSNK(N-Me)GA(N-Me)II, NK(N-Me)GA(N-Me)IIGL, GSNK(N-Me)GA(N-Me)II, G(N-Me)AI(N-Me)I, KG(N-Me)AI(N-Me)I, NKG(N-Me)AI(N-Me)I, SNKG(N-Me)AI(N-Me)I, GSNKG(N-Me)AI(N-Me)I, NKG(N-Me)AI(N-Me)IGL, GSNKG(N-Me)AI(N-Me)IGL, KGA(N-Me)II, NKGA(N-Me)II, SNKGA(N-Me)II, GSNKGA(N-Me)IIGL, GS(N-Me)NKGAIIGL, and (N-Me)GS(N-Me)NKGAIIGL, (N-Me)GS(N-Me)GAIIGL.

8. A peptide selected from the group consisting of (N-Me)GA(N-Me)VV, A(N-Me)GA(N-Me)VV, AA(N-Me)GA(N-Me)VV, AAGA(N-Me)VVGG, HV(N-Me)AAGAVVGG, (N-Me)HV(N-Me)AAGAVVGG, and (N-Me)HV(N-Me)AA(N-Me)GAVVGG.

9. A peptide selected from the group consisting of GAIL, SEQ ID NO: 1; FGAIL, SEQ ID NO: 2; NFGAIL, SEQ ID NO: 3; NNFGAIL, SEQ ID NO: 4; SNNFGAIL, SEQ ID NO: 5; NFGAILSS, SEQ ID NO: 6; SNNFGAILSS, SEQ ID NO: 7; GAII, SEQ NO: 8; KGAII, SEQ ID NO: 9; NKGAII, SEQ ID NO: 10; SNKGAII, SEQ ID NO: 11; GSNKGAII, SEQ ID NO: 12; NKGAIIGL, SEQ ID NO: 13; GSNKGAIIGL, SEQ ID NO: 14; GAVV, SEQ ID NO: 15; AGAVV, SEQ ID NO: 16; HVAAGAVV, SEQ ID NO: 18; AAGAVVGG, SEQ ID NO: 19; HVAAGAVVGG, SEQ ID NO: 20; and AAGAVV, SEQ ID NO: 21, wherein the H-atom at every second amide bond is optionally replaced by a methyl group, and the number of methylated amide bonds varies between one and half of the amide bonds in the peptide.

10. A peptide comprising 3–15 amino acids and said peptide contains a peptide sequence selected from the group consisting GAIL, SEQ ID NO: 1; FGAIL, SEQ ID NO: 2; NFGAIL, SEQ ID NO: 3; NNFGAIL, SEQ ID NO: 4; SNNFGAIL, SEQ ID NO: 5; NFGAILSS, SEQ ID NO: 6; SNNFGAILSS, SEQ ID NO: 7; GAII, SEQ ID NO: 8; KGAII, SEQ ID NO: 9; NKGAII, SEQ ID NO: 10; SNKGAII, SEQ ID NO: 11; GSNKGAII, SEQ ID NO: 12; NKGAIIGL, SEQ ID NO: 13; GSNKGAIIGL, SEQ ID NO: 14; GAVV, SEQ ID NO: 15; AGAVV, SEQ ID NO: 16; HVAAGAVV, SEQ ID NO: 18; AAGAVVGG, SEQ ID NO: 19; HVAAGAVVGG, SEQ ID NO: 20 and AAGAVV, SEQ ID NO: 21, wherein the H-atom at every second amide bond is optionally replaced by a methyl group, and the number of methylated amide bonds varies between one and half of the amide bonds in the peptide.

* * * * *